United States Patent [19]

Sato et al.

[11] Patent Number: 5,232,947
[45] Date of Patent: Aug. 3, 1993

[54] OXAMIC ACID COMPOUNDS AND PHARMACEUTICAL COMPOSITION FOR USE IN IMPROVEMENT OF DAMAGED CEREBRAL FUNCTIONS OF BRAIN

[75] Inventors: Yasuo Sato; Shinsuke Katoh; Kunio Atsumi; Mitsugu Hachisu; Seiji Shibahara, all of Yokohama, Japan

[73] Assignee: Meiji Seika Kaisha, Ltd., Japan

[21] Appl. No.: 754,393

[22] Filed: Sep. 4, 1991

Related U.S. Application Data

[62] Division of Ser. No. 373,469, Jun. 30, 1989, abandoned.

[30] Foreign Application Priority Data

Jul. 4, 1988 [JP] Japan .................. 63-164938

[51] Int. Cl.$^5$ .................. C07C 229/00; A61K 31/22
[52] U.S. Cl. .................. 514/549; 514/551; 514/921; 562/553; 562/571
[58] Field of Search .............. 562/571, 553; 514/921, 514/549, 551

[56] References Cited

U.S. PATENT DOCUMENTS

| 3,956,069 | 5/1976 | Allain et al. | 195/103.5 |
| 4,950,602 | 8/1990 | Cooper | 435/184 |
| 4,960,701 | 10/1990 | Horiuchi et al. | 435/190 |

FOREIGN PATENT DOCUMENTS 1270552 6/1988 Fed. Rep. of Germany.

OTHER PUBLICATIONS

Danilov, G. E. *Chem. Abs.* 72(15) 77219x (1970).
Naumov, Y. U. *Chem. Abs.* 86(17):120763y (1977).
Nippon Kayaku, *Patent Abs. of Japan* 3 (50):C-44 1979.
Ube Kosan, *Patent Abs. of Japan* 9(21):C-263, 1744 (1985).
Broniszewska—Ardelt, B. et al., Bulletin De L'Academie Polonaise Des Sciences 23(7):505–512 (1975).
Vorel, F. et al. Physiologica Bohemslovaca 17:411–415 (1968).
Belasco, I. J. et al. J. Agric. Food Chem. 28:689–92 (1980).
Wakita, Y. et al. J. Organometallic Chem. 297:379–390 (1985).
Vermeulen, N. M. J. et al. South Afrkan J. of Science 77:566–569 (1981).
Penny, J. E. et al. Proc. Australian Assoc. of Neurologists 11:177–181 (1974).

Primary Examiner—Richard L. Raymond
Assistant Examiner—Gary E. Hollinden
Attorney, Agent, or Firm—Lalos & Keegan

[57] ABSTRACT

New N,N-di-alkyl- or alkenyl-substituted derivatives of oxamic acid of which the two alkyl or alkenyl groups are different from each other are now produced and found to exhibit the cerebral protective effect against cerebral anoxia in the brain of a mammalian animal, including human, and to be useful as an agent for improving or ameliorating the damaged or disturbed functions of the brain. Some known N,N-di-alkyl-substituted derivatives of oxamic acid or which the two alkyl groups are identical to each other are now also found to have similar, cerebral protective effect against cerebral anoxia and to be useful as an agent for improving the damaged functions of the brain.

3 Claims, No Drawings

OXAMIC ACID COMPOUNDS AND PHARMACEUTICAL COMPOSITION FOR USE IN IMPROVEMENT OF DAMAGED CEREBRAL FUNCTIONS OF BRAIN

This is a divisional of copending application Ser. No. 07/373,469 filed on Jun. 30, 1989, now abandoned.

SUMMARY OF THE INVENTION

This invention relates to new and useful oxamic acid compounds, particularly new N,N-di-substituted derivatives of oxamic acid which exhibit cerebral protective effect against cerebral anoxia (a reduced oxygen-supply from the blood) as induced in the brain of a mammalian animal, including human, by subjecting it to hypoxic conditions, and which owing to their cerebral protective effect, have medicinal effects of improving or ameliorating different symptoms of cerebral disorders or diseases caused by damaged or disturbed intracerebral energy metabolism. This invention also relates to a pharmaceutical composition comprising as the active ingredient said new oxamic acid compound or known analogous oxamic acid compound having similar medicinal effects. This pharmaceutical composition is of particular utility as a drug for improving or ameliorating the damaged or disturbed cerebral functions of the brain of a mammalian animal, including human. This invention also includes new medicinal use of the N,N-di-substituted oxamic acid compound. Furthermore, this invention relates to a process for the preparation of the new and useful oxamic acid compounds.

BACKGROUND OF THE INVENTION

Reflecting the advent of the so-called "high-age" society, it has become a serious public concern to develop medical measures for treatment of senile dementia as caused by damages or disturbances of the cerebral functions which are, in turn, attributable to cerebrovascular diseases or damages or disturbances of intracerebral energy metabolism. A variety of drugs has heretofore been developed as anti-dementia drugs. At the present time, senile dementia, amnesia as caused by cerebrovascular diseases and the biological mechanisms of occurrence of these disorders or diseases have not yet been elucidated fully. In these circumstances, no sufficient clue has yet been established to discover and screen effective cerebral drugs. As experimental methods for inducing amnesia in normal mammalian animals, it is known to administer such an agent which inhibits the in vivo synthesis of nucleic acids or proteins, or an anticholinergic agent. Amnesia is also known to be inducible by cerebral anoxia, ischemic load or the like. With using such model animals which have amnesia induced by these causative agents, it has been attempted to detect and develop cerebral drugs which are capable of amelioractively treating or preventing the amnesia. In addition, when using such model animals which have cerebral anoxia induced either by giving a lethal dose of potassium cyanide or by subjecting to hypobaric or normabaric hypoxic conditions, namely, the reduced oxygen-supply conditions, attempts have also been made to develop cerebral drugs which are effective for the improvement or amelioration of cerebral circulation metabolism or intracerebral energy metabolism. These matters are related to e.g. in "Folia Pharmacol. Japan", 85, 323-328 (1985); ibid., 86, 445-456 (1986): and Japanese Patent Application first publication "Kokai" No. 117468/79 or its corresponding U.S. Pat. No. 4,369,139.

It is well accepted that oxygen deprivation is one of the most damaging conditions affecting the animal or human brain, and that when oxygen supply tot he brain becomes deficient, cerebral functions cease after brief periods of cerebral anoxia and tissue destruction ensues. Consequently, any suitable agents which enable the brain to withstand even mild degrees of cerebral anoxia would be expected to be useful as a cerebral protective agent or a drug for improving or ameliorating the damaged or disturbed cerebral functions of the brain (the drug of this utility is hereinafter sometimes merely called "a cerebral drug"). Many compounds have been investigated for their cerebral protective effect on cerebral anoxia which is experimentally induced by subjecting the animal to hypoxic conditions, whereby there is obtained a suggestion or indication that the tested compounds are effective for treatment of cerebral anoxic or ischemic diseases or disorders (see, e.g. "Arch. int. Pharmacodyn."233, 136-144 (1978) and "Life Science" 13, 467-474 (1973)).

However, the cerebral drugs which have been provided so far can hardly be said to have fully satisfactory effects and proven reliability. Under these circumstances, there remains a demand for the development of new cerebral drugs which are still stronger and safer than the known drugs as provided to date.

On the other hand, Japanese Patent Application first publication "Kokai" No. 24823/79 discloses a process for the preparation of N,N-di-substituted glycol amides which have the utility as stabilizers or solvents for polymers. It is described there that N,N-di-substituted oxamic acids are formed as by-products in said process. Specific compounds whose formation as the by-products were confirmed in the process of the above patent publication are limited to N,N-dimethyloxamic acid, N,N-diethyloxamic acid, N,N-di-n-propyloxamic acid, N,N-di-n-butyloxamic acid, N,N-di-allyloxamic acid, N,N-cyclopentyloxamic acid, N-methyl-N-phenyloxamic acid and N,N-diphenyloxamic acid. The above patent publication discloses neither utility of these N,N-di-substituted oxamic acids nor their physiological activities. Further, N,N-di-isopropyloxamic acid is disclosed in the "Journal of Organometallic Chemistry" 297, 379-390 (1985) but its physiological activities are not reported at all there.

An object of this invention is to prepare and provide novel compounds having excellent pharmacological effects for the improvement of the damaged or disturbed cerebral functions of the brain as well as a high level of safety and being free of side effects. Another object of this invention is to provide novel cerebral drugs. To achieve these objects, we, the present inventors, have proceeded with extensive investigations. As a result, we have now found 'hat compounds having anti-anoxia effects, in other words, cerebral protective effect against cerebral anoxia, are useful or promising as drugs having medicinal effects capable of treating cerebration disorders of mammals, including human, when such compounds are effective in significantly prolonging the survival time of mice having cerebral anoxia experimentally induced under hypobaric hypoxia conditions in the experiments wherein the cerebral anoxia mice are used as model animals. We, the present inventors, have thus been interested in some N,N-dialkyloxamic acids (which may also be called N,N-dialkyloxaminic acids) which are disclosed in Japanese Patent Application first publication "Kokai" no. 24823/79, and we have tested the cerebral protective effect of these known compounds against cerebral anoxia. Moreover, we have also synthesized novel N,N-di-substituted oxamic acid compounds which had not been reported in any prior art publications, and we have assayed the cerebral protective effect of these novel compounds against cerebral anoxia.

As a result of our above investigations and tests, we have found that N,N-di-substituted oxamic acid compounds which include a class of novel oxamic acid compounds having the below-described formula (Ia) and which may generally be represented by the below-described formula (I) have the cerebral protective effect against cerebral anoxia and low toxicity. Their potential usefulness as the cerebral drugs has also been ascertained.

In addition, we have also succeeded in providing a process which can advantageously produce the novel compounds of the formula (Ia) on a commercial scale.

DETAILED DESCRIPTION OF THE INVENTION

In a first aspect of this invention, therefore, there is provided as the new compounds an oxamic acid compound having the general formula

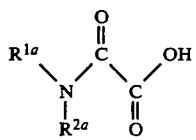

(Ia)

wherein $R^{1a}$ and $R^{2a}$ are different from each other and are individually a linear of branched alkyl group of 1 to 4 carbon atoms or an alkenyl group of 2 to 4 carbon atoms, or a pharmacologically acceptable salt thereof.

In a second aspect of this invention, there is provided a pharmaceutical composition comprising an oxamic acid compound having the general formula

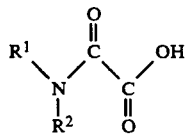

(I)

wherein $R^1$ and $R^2$ may be the same or different and are individually a linear or branched alkyl group of 1 to 4 carbon atoms or an alkenyl group of 2 to 4 carbon atoms, or a pharmacologically acceptable salt thereof as an active ingredient, in association with a pharmaceutically acceptable solid or liquid carrier for the active ingredient.

In particular, the pharmaceutical composition of the second aspect of this invention may be used for improving or ameliorating the damaged cerebral functions of the brain of a mammalian animal, and it may also be used as a cerebral protective agent, especially for protection against anoxic brain damage in a mammalian animal or for improvement or amelioration of the damaged cerebral functions of the brain in a mammalian animal as induced due to low oxygen supply.

In a third aspect of this invention, there is provided a method for protecting against anoxic brain damage in a mammalian animal, which comprises parenterally or orally administering a pharmacologically effective amount of an oxamic acid compound having the formula (I)

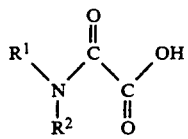

(I)

wherein $R^1$ and $R^2$ are the same or different and are individually a linear or branched alkyl group of 1 to 4 carbon atoms or an alkenyl group of 2 to 4 carbon atoms, or a pharmacologically acceptable salt thereof, to the animal.

In a further aspect of this invention, there is provided a method for improving or ameliorating the damaged cerebral functions of the brain in a mammalian animal as induced due to low oxygen supply, which comprises parenterally or orally administering a pharmacologically effective amount of an oxamic acid compound having the formula (I) as defined in the above or a pharmacologically acceptable salt thereof, to the animal.

When the compound of the formula (I) is administered to the animal or human to be treated, it may be given parenterally, for example, intramuscularly, intravenously, intraperitoneally, subcutaneously, rectally, or orally.

This invention further includes use of the oxamic acid compound having the formula (I) defined in the above or a pharmacologically acceptable salt thereof, as a cerebral protective agent, especially as an agent for protecting against anoxic brain damage in a mammalian animal, or as an agent for improving or ameliorating the damaged cerebral functions of the brain of a mammalian animal as induced by disturbance of the cerebral energy metabolism.

For the N,N-di-substituted derivatives of oxamic acid having the general formulae (Ia) and (I) according to this invention, specific examples of the linear or branched alkyl group of 1–4 carbon atoms and alkenyl group of 2–4 carbon atoms, which are represented by $R^{1a}$ and $R^{2a}$ in the compound of the formula (Ia) and also by $R^1$ and $R^2$ in the compound of the formula (I) include methyl, ethyl, n-propyl, iso-propyl, n-butyl, iso-butyl, sec-butyl, tert-butyl, and the like; and allyl, methallyl, crotyl, and the like.

Suitable examples of the new compound of the formula (Ia) according to the first aspect of this invention include N-ethyl-N-n-propyloxamic acid, its sodium or potassium salt; N-ethyl-N-isopropyloxamic acid, its sodium or potassium salt; N-ethyl-N-n-but·˙loxamic acid, its sodium or potassium salt; and N-ethyl-N-isobutyloxamic acid, its sodium or potassium salt. The compounds of the general formula (I) usable according to the second aspect of this invention embrace the new compound of the formula (Ia), as well as the aforesaid known derivatives of oxamic acid which are N,N-dimethyloxamic acid, N,N-diethyloxamic acid, N,N-di-n-propyloxamic acid, N,N-di-isopropyloxamic acid, N,N-di-n-butyloxamic acid and N,N-di-allyloxamic acid and which may collectively be represented by the general formula

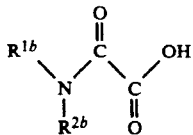

(Ib)

wherein $R^{1b}$ and $R^{2b}$ are the same and selected from methyl, ethyl, n-propyl, isopropyl, n-butyl, and allyl groups.

Illustrative examples of the pharmacologically acceptable salt of the compound having the formula (Ia) or (I) according to this invention include a salt of the carboxyl group of the compound with a pharmaceutically acceptable metal, especially conventional non-toxic salts, for example, alkali metal salts such as the sodium salt and potassium salt, alkaline earth metal salts such as the calcium salt and magnesium salt, and the ammonium salt. Also mentioned are additional salts with organic bases, for example, salts with low alkylamines such as triethylamine, additional salts with organic amines such as the pyridine, ethanolamine, triethanolamine and dicyclohexylamine salts, and additional salts with basic amino acids such as arginine.

The novel compounds of the formula (Ia) according to this invention can each be prepared by such a process which comprises hydrolyzing an oxamic acid ester compound having the formula (II) shown below, according to the following reaction equation:

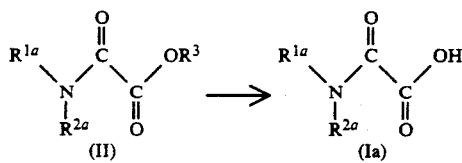

wherein $R^{1a}$ and $R^{2a}$ are different from each other and mean individually a linear or branched alkyl group having 1–4 carbon atoms or an alkenyl group having 2–4 carbon atoms, and $R^3$ denotes a linear or branched alkyl group having 1–4 carbon atoms, an aralkyl group such as benzyl or an aryl group such as phenyl.

In another aspect of this invention, therefore, there is provided a process for the preparation of the oxamic acid compound having the formula (Ia) defined in the above, which comprises hydrolyzing an oxamic acid ester compound having the following formula (II)

wherein $R^1$ and $R^2$ are different from each other and are individually a linear or branched alkyl group of 1 to 4 carbon atoms or an alkenyl group of 2 to 4 carbon atoms, and $R^3$ denotes a linear or branched alkyl group of 1 to 4 carbon atoms, an aralkyl group or an aryl group.

Specific examples of the linear or branched alkyl group of 1–4 carbon atoms, which is represented by $R^{1a}$ and $R^{2a}$ in the starting ester compound of the formula (II), include methyl, ethyl, n-propyl, iso-propyl, n-butyl, iso-butyl, sec-butyl and tert-butyl. Further specific examples of the alkenyl group as represented by $R^{1a}$ and $R^{2a}$ in the starting ester compound of the formula (II) include allyl, methallyl, crotyl, and the like. Specific examples of the linear or branched alkyl group of 1–4 carbon atoms represented by $R^3$ include methyl, ethyl, n-propyl, iso-propyl, n-butyl, iso-butyl, sec-butyl, tert-butyl, and the like. On the other hand, illustrative examples of the aralkyl group represented by $R^3$ include phenyl-$(C_1–C_4)$-alkyl groups such as benzyl and phenethyl. Further, exemplary aryl groups represented by $R^3$ include unsubstituted or substituted phenyl groups.

The hydrolytic reaction of the starting ester compound of the formula (II) may be conducted at $-10°$ C. to $50°$ C., for 0.1 hours to several hours, in the presence of a base, in water or an aqueous organic solvent. Examples of the organic solvent include alcohols such as methanol, ethanol and propanol; and aprotonic solvents such as 1,4-dioxane, tetrahydrofuran and pyridine. As exemplary bases, may be mentioned alkali metal hydroxides such as sodium hydroxide and potassium hydroxide; alkaline earth metal hydroxides such as magnesium hydroxide and calcium hydroxide; quaternary ammonium hydroxides such as tetrabutyl ammonium hydroxide and benzyl trimethyl ammonium hydroxide; alkali metal carbonates such as sodium carbonate and potassium carbonate; tertiary amines such as trialkylamines, e.g., triethylamine, N-methylpiperidine and 4-(N,N-dimethylamino)pyridine; etc.

The starting ester compound having the formula (II) can be prepared, for example, by such a method in which an amine compound of the formula (III) is condensed with a (chloroformyl) formic acid ester of the formula (IV) shown below, according to the following reaction equation:

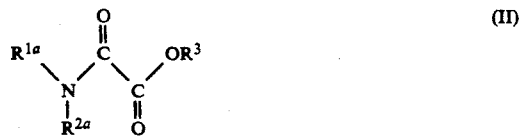

(II)

wherein $R^{1a}$, $R^{2a}$ and $R^3$ have the same meanings as defined above.

The toxicity of the compounds of the general formula (I) usable in this invention was evaluated by using N,N-di-isopropyloxamic acid as one example. When 3 ddy mice (male, 5 weeks-old, body weight: 25 g) in each group were administered intravenously with a dose of 1000 mg/kg of the test compound, all the mice tolerated it and remained alive, thereby demonstrating that the compounds usable in this invention have low toxicity and are useful as cerebral protective agents or as agents for therapeutically treating and improving the damaged cerebral functions of the mammalian animal brain.

The pharmaceutical composition according to this invention which comprises one or more of the compounds of the general formula (I) and a salt thereof as the active ingredient may be formulated into various preparation forms, primarily, as injections such as intravenous injections, oral preparations such as capsules, tablets and powders, rectal preparations, fat-and-oil base suppositories, water-soluble suppositories, etc. These various preparations can be produced in a manner known per se in the art, using one or more of excipients, extenders, binders, wetting agents, disintegrators, surfactants, lubricants, dispersants, buffers, preservatives, solubilizers, antiseptics, corrigents, soothing agents and the like. Specific illustrative methods of preparing some preparations will be described in Examples 7-9 given hereinafter.

The dose of each compound of the formula (I) can be suitably determined for each case by taking into consideration the symptom, age, sec, etc. of patients to be treated. For a general guideline, the daily dose of the compound may range from 250 mg to 3000 mg per adult. This dose may usually be administered in 1-4 portions a day.

TEST 1

The cerebral protective effect of the improving or ameliorative effect on the damaged cerebral functions of the oxamic acid compounds of formula (I) of this invention was examined in terms of their effect that can prolong the survival time of such mice having cerebral anoxia experimentally induced under the load of hypobaric hypoxia.

ddy Mice (6 weeks old, body weight: 25–30 g, each group comprising 6 ddy mice) were administered intraperitoneally with the compounds of the present invention, respectively. Each of the tested compounds of this invention had been beforehand dissolved in redistilled water and the aqueous solution was administered in an amount of 0.1 ml per 10 g body weight. Thirty minutes after the administration, the mice were individually placed in hermetic transparent containers. The containers were rapidly evacuated to 190 mmHg by means of a vacuum pump. Time was measured from the initiation of the evacuation to the death of each mouse due to respiratory failure. That time was recorded as the survival time (seconds) of mice.

The ratios of the survival time of the groups of the treated mice which received the administration of the tested compounds of this invention divided by the survival time of a control group (untreated) which received no administration of the drug were calculated. The ratios are shown in Table 1 below.

anoxia induced by conditions of hypobaric hypoxia and hence exhibit protective effects against cerebral anoxia.

It is believed that the compounds of the formula (I) according to this invention have the activities of improving or ameliorating the cerebral energy mechanism and circulation in a mammalian animal because they have the effects of promoting the supply of oxygen from blood to the brain, reducing the wasteful consumption of oxygen and ATP in the brain and enhancing the formation of ATP in the brain.

In clinical applications, the compounds of the formula (I) of this invention are believed to be effective especially for the improvement of hypobulia, emotional troubles and the like, which tend to occur as sequela of cerebral infarction, intracerebral bleeding, etc. They are also believed to be effective as therapeutic agents for senile dementia in view of their effectiveness of the improvement of hypobulia.

The present invention will hereinafter be illustrated by the following Referential Synthesis Examples 1-2 which show the preparation of certain starting esters of formula (II), and also by the following Examples 1-6 which show the production of certain compounds of formula (I) according to this invention.

REFERENTIAL SYNTHESIS EXAMPLE 1

Synthesis of methyl N-ethyl-N-n-propyloxamate

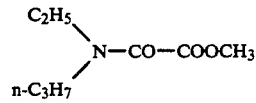

On gram (11.5 mmole) of N-ethyl-N-n-propylamine was added to 30 ml of methylene chloride. The resulting mixture was stirred under cooling at −78° C. over a dry-ice/acetone bath, followed by the dropwise addition of 703 mg (5.7 mmole) of methyl (chloroformyl)formate. While gradually raising the temperature of the reaction vessel up to room temperature, the reaction mixture was stirred for 2 hours. The reaction solution was then poured into ice-water, followed by extracting with 70 ml of methylene chloride. The organic layer (the extract) was washed successively with a 10% aqueous solution of citric acid, water, a saturated aqueous solution of sodium hydrogen carbonate, water and saturated saline. Anhydrous magnesium sulfate was then

TABLE 1

| Name of test compound | Structure of test compound | Dose of test compound (mg/kg) | Survival time ratio (control group: 100) |
|---|---|---|---|
| N-ethyl-N-n-propyl-oxamic acid | $C_2H_5$<br>$\phantom{xx}\diagdown$<br>$\phantom{xxxxx}N-CO-COOH$<br>$\phantom{xx}\diagup$<br>$n-C_3H_7$ | 100 | 166 |
| N-ethyl-N-butyl-oxamic acid | $C_2H_5$<br>$\phantom{xx}\diagdown$<br>$\phantom{xxxxx}N-CO-COOH$<br>$\phantom{xx}\diagup$<br>$n-C_4H_9$ | 100 | 116 |
| N,N-di-isopropyl-oxamic acid | $(iso\text{-}C_3H_7)_2-N-CO-COOH$ | 100 | 155 |
| N,N-di-n-propyl-oxamic acid | $(n\text{-}C_3H_7)_2-N-CO-COOH$ | 100 | 181 |
| N,N-di-allyloxamic acid | $(CH_2=CH-CH_2)_2-N-CO-COOH$ | 100 | 187 |

As is apparent from the foregoing tests, the compounds of formula (I) of this invention can significantly prolong the survival time of animals having cerebral added to the organic layer to dry same. The organic layer was filtered and then concentrated under reduced pressure, thereby obtaining 955 mg (5.5 mmole) of methyl N-ethyl-N-n-propyloxamate as a colorless oil.

$^1$H-NMR, δ (CDCl$_3$):
0.90 (3H,dt,J=8Hz, 3Hz), 1.19 (3H,dt,J=7Hz,3Hz), 1.62 (2H,sext,J=7Hz), 3.05-3.53 (4H,m).

REFERENTIAL SYNTHESIS EXAMPLE 2

Synthesis of methyl N-ethyl-N-n-butyloxamate

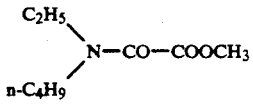

When using N-ethyl-N-n-burylamine as a starting compound for its reaction with methyl (chloroformyl) formate, the title compound was obtained in a similar manner to Referential Synthesis Example 1.

$^1$H-NMR, δ (CDCl$_3$):
0.92 (3H,t,J=7Hz), 1.19 (3H,dt,J=7Hz,3Hz), 1.15-1.90 (4H,m), 3.50-3.60 (4H,m).

EXAMPLE 1

Preparation of N-ethyl-N-n-propyloxamic acid

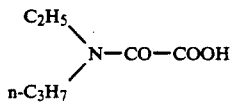

870 mg (5.0 mmole) of methyl N-ethyl-N-n-propyloxamate was dissolved in 20 ml of methanol. The resulting mixture was stirred under ice-cooling over an ice bath. 594 mg (15 mmole) of sodium hydroxide was dissolved in 10 ml of water and the resulting solution was added dropwise to said mixture. After completion of the dropwise addition, the ice bath was removed and the reaction mixture was stirred for 1 hour at room temperature. After adding 10 ml of 1N aqueous solution of hydrochloric acid, the solvent was distilled off from the reaction solution under reduced pressure. The residue was added with 80 ml of ethanol and the insoluble solids as formed were filtered off. The organic solution after the filtration was concentrated to afford 305 mg (1.9 mmole) of N-ethyl-N-n-propyloxamic acid as a colorless oil.

$^1$HMR, δ (D$_2$O):
0.93 (3H,t,J=7Hz), 1.22 (3H,dt,J=7Hz,6Hz), 1.40-2.00 (2H,m), 3.10-3.60 (2H,m).

IR absorption (cm$^{-1}$, neat):
1635, 1440, 1230, 1200, 1145.

EXAMPLE 2

Preparation of N-ethyl-N-n-butyloxamic acid

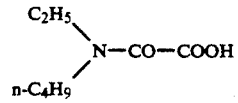

From methyl N-ethyl-N-n-butyloxamate, the title compound was synthesized in a similar manner to Example 1.

$^1$H-NMR, δ (D$_2$O$_3$):
0.70-1.20 (3H,m), 1.00-1.90 (7H,m),
3.41 (2H,t,J=7Hz), 3.46 (2H,q,J=7Hz)

IR absorption (cm$^{-1}$, neat)
1710, 1630, 1460, 1380, 1280, 1250.

EXAMPLE 3

Preparation of sodium N-ethyl-N-n-propyloxamate

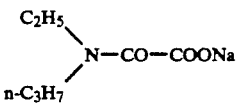

475 mg (2.75 mmole) of methyl N-ethyl-N-n-propyloxamate was dissolved in 10 ml of methanol. The resulting mixture was stirred under ice-cooling. 109 mg (2.75 mmole) of sodium hydroxide was dissolved in 5 ml of water, and the resulting solution was added dropwise to said mixture. After completion of the dropwise addition, the reaction mixture was stirred for 3 hours at room temperature. Methanol was distilled off from the reaction solution under reduced pressure and the remaining aqueous layer was washed with 5 ml of methylene chloride. The aqueous layer was then separated and distilled under reduced pressure, to afford 495 mg (2.7 mmole) of sodium N-ethyl-N-n-propyloxamate as white solids.

$^1$H-NMR, δ (D$_2$O):
3.75-3.20 (4H,m), 2.10-1.35 (2H,m), 1.50-1.00 (3H,m), 1.20-0.75 (3H,dt,J=8Hz,2Hz).

EXAMPLE 4

Preparation of N,N-di-isopropyloxamic acid

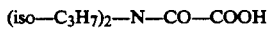

(a) One gram (9.9 mmole) of N,N-di-isopropylamine was added to 30 ml of methylene chloride. The resulting mixture was stirred under cooling at −78° C. over a dry ice-acetone bath, followed by the dropwise addition of 605 mg (4.9 mmole) of methyl (chloroformyl) formate. While gradually raising the temperature of the reaction vessel up to room temperature, the reaction mixture was stirred for 2 hours. The resulting reaction solution was then poured into ice water and extracted with 70 ml of methylene chloride. The organic layer (the extract) was washed successively with a 10% aqueous solution of citric acid, water, a saturated aqueous solution of sodium hydrogen carbonate, water and saturated saline. Anhydrous magnesium sulfate was then added to the organic layer to dry same. The organic layer was filtered and then concentrated under reduced pressure, to give 800 mg (4.3 mmole) of methyl N,N-di-isopropyloxamate as a colorless oil.

550 mg of methyl N,N-di-isopropyloxamate was dissolved in 20 ml of methanol. The resulting solution was stirred under ice-cooling, to which 15 ml of 1N aqueous solution of sodium hydroxide was added dropwise. After completion of the dropwise addition, the resultant mixture was stirred for 1 hour at room temperature. The solvent was distilled off from the resulting reaction solution under reduced pressure. The residue was added with 20 ml of 1N HCl. Insoluble white precipitates were collected by filtration, washed with chilled water and n-hexane, and then dried to obtain 180 mg of the title compound, N,N-di-isopropyloxamic acid as white solids.

$^1$H-NMR, δ (CD$_3$OD):

1.23 (6H,d,J=7Hz), 1.40 (6H,d,J=7Hz),
3.40–4.00 (2H,m).
IR absorption (cm$^{-1}$, KBr):
1720, 1565, 1370, 1230, 1190.

EXAMPLE 5

Preparation of N,N-di-n-propyloxamic acid

N,N-di-n-propyloxamic acid was obtained by initiating the reaction of N,N-di-no-propylamine with methyl (chloroformyl) formate, in a similar manner to Example 4.

$^1$H-NMR, δ (CDCl$_3$):
0.92 (6H,t,J=7Hz), 1.30–1.90 (4H,m),
3.35 (2H,t,J=7Hz), 3.66 (2H,t,J=7Hz),
5.94 (1H,broad).
IR absorption (cm$^{-1}$, Nujol);
1730, 1600, 1265, 1125.

EXAMPLE 6

Preparation of N,N-di-allyloxamic acid

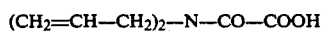

(CH$_2$=CH—CH$_2$)$_2$—N—CO—COOH (a) One gram of N,N-di-allylamine was added to 30 ml of methylene chloride. The resulting mixture was stirred under cooling at −78° C. over a dry-ice/acetone bath, followed by the dropwise addition of 630 mg of methyl (chloroformyl) formate. While gradually raising the temperature of the reaction vessel up to room temperature, the reaction mixture was stirred for 2 hours. The resulting reaction solution was then poured into ice water and extracted with 70 ml of methylene chloride. The organic layer (the extract) was washed successively with a 10% aqueous solution of citric acid, water, a saturated aqueous solution of sodium hydrogen carbonate, water an saturated saline. Anhydrous magnesium sulfate was then added to the organic layer to dry same. The organic layer was filtered and then concentrated under reduced pressure, to give 875 mg of methyl N,N-di-allyloxamate as a colorless oil.

$^1$H-NMR, δ (CDCl$_3$):
3.85 (3H,s), 4.07–4.36 (4H,m),
4.98–5.33 (4H,m), 5.49–6.00 (2H,m)

(b) 600 mg of methyl N,N-di-allyloxamate was dissolved in 20 ml of methanol. The resulting solution was stirred under ice-cooling, to which 15 ml of 1N aqueous solution of sodium hydroxide was added dropwise. After completion of the dropwise addition, the resultant mixture was stirred for 1 hour at room temperature. The resulting reaction solution was distilled to a volume of about 10 ml at room temperature under reduced pressure. The concentrated solution was adjusted to pH 4 by addition of 1N HCl, followed by extraction with 50 ml of ethyl acetate. The extract solution was washed with saturated saline and dried over anhydrous sodium sulfate added. After filtration, the organic layer (the solution) was concentrated under reduced pressure, to afford 460 mg of the title compound, N,N-di-allyloxamic acid as white solids.

$^1$H-NMR, δ (CD$_3$CL$_3$):
4.03 (2H,d,J=7Hz), 4.18 (2H,d,J=7Hz)
5.10–5.40 (4H,m), 5.65–5.95 (2H,m)
10.23 (1H,s)
IR absorption (cm$^{-1}$, Nujol):
1735, 1640, 1500, 1420, 1300, 1288, 1210

Methods for preparing various formulations will now be described in the following Examples. It should however be borne in mind that the invention is not necessarily limited thereto.

EXAMPLE 7

One part (by weight) of N,N-di-isopropyloxamic acid, 2.7 parts (by weight) of lactose, 0.8 parts (by weight) of corn starch and 0.05 parts (by weight) of polyvinylpyrrolidone were mixed. The resultant mixture was wetted with ethanol and granulated by a conventional method, dried, screened, and then admixed with 0.5% of magnesium stearate. The resultant mixture was formed into 100 mg-tablets in a manner known per se in the art.

EXAMPLE 8

Five grams of N,N-di-isopropyloxamic acid and 5 g of mannitol were dissolved in distilled water to give a total volume of 1000 ml. After sterilizing the aqueous solution in a manner known per se in the art, it was filled in 2 ml-portions into vials and then lyophilized. Upon use, the lyophilized preparation was dissolved in sterile distilled water to prepare an injectable solution.

EXAMPLE 9

One part (by weight) of N,N-di-isopropyloxamic acid and 4 parts (by weight) of lactose were mixed thoroughly and then sifted through a 50 mesh sieve to prepare a powder formulation.

We claim:

1. A method for ameliorating damaged cerebral functions of the brain in a mammal as induced by cerebral anoxia, which comprises administering intravenously, intraperitoneally, orally intramuscularly, subcutaneously or rectally to a mammal having the damaged cerebral functions an N,N-di-substituted oxamic acid compound having the formula (I)

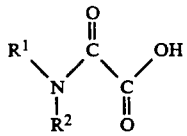

wherein R$^1$ and R$^2$ may be the same or different and are individually a linear or branched alkyl group of 1 to 4 carbon atoms or an alkenyl group of 2 to 4 carbon atoms, or a pharmacologically acceptable salt thereof, in an amount effective to ameliorate the damaged cerebral functions.

2. A method for ameliorating damaged cerebral functions of the brain in a mammal as induced by cerebral anoxia, which comprises administering intravenously, intraperitoneally, orally, intramuscularly, subcutaneously or rectally to a mammal having the damaged cerebral functions an N,N-di-substituted oxamic acid compound selected from N,ethyl-N-n-propyloxamic acid; N-ethyl-N-isopropyloxamic; N-ethyl-N-n-butyloxamic acid; N-ethyl-N-isobutyloxamic acid; N,N-dimethyloxamic acid; N,N-di-ethyloxamic acid; N,N-di-n-propyloxamic acid, N,N-di-isopropyloxamic acid, N,N-di-n-butyloxamic acid; N,N-di-allyloxamic acid and pharmacologically acceptable salts thereof, in an amount effective to ameliorate the damaged cerebral functions.

3. A method as claimed in claim 2 in which there is administered one N,N-di-substituted oxamic acid compound selected from N-ethyl-N-n-propyloxamic acid; N,N-di-isopropyloxamic acid; N,N-di-n-propyloxamic acid; N,N-di-allyloxamic acid and pharmacologically acceptable salts thereof.

* * * * *